United States Patent [19]
Folkman et al.

[11] Patent Number: 5,229,493
[45] Date of Patent: Jul. 20, 1993

[54] SMOOTH MUSCLE MITOGEN

[75] Inventors: Moses J. Folkman, Brookline; Yuen Shing, Randolph, both of Mass.

[73] Assignee: Children's Medical Center Corporation, Boston, Mass.

[21] Appl. No.: 604,778

[22] Filed: Oct. 26, 1990

[51] Int. Cl.$^5$ .......................... C07K 3/20; C07K 15/06
[52] U.S. Cl. .................................. 530/350; 530/116; 530/417; 530/845
[58] Field of Search .................... 514/12, 21; 530/350, 530/416, 417, 845

[56] References Cited

U.S. PATENT DOCUMENTS 4,785,079 11/1988 Gospodarowicz et al. ......... 530/416
4,889,919 12/1989 Murray et al. ...................... 530/375

OTHER PUBLICATIONS

Spier et al, *Animal Cell Biotechnology*, Academic Press, 1985, pp. 10–11.
Schwartz, et al. Circulation Research vol. 58 No. 4 p. 427 (1986).
Ross and Glomset N. Engl. J. Med. 295:369–377 (1976).
Oka & Orth, J. Clin. Inves. 72:249–259 (1983).
Tucker, et al. Science 266:705–777 (1984).
Kohler G. et al., Nature 256:495–497 (1975).
Huse, et al. Science 246:1275–1281 (1989).
Shing, Y. Davison, S. and Klagsbrun, M. Methods in Enzymology 146 42–48, (1987).
Yung-Chin Wang et al., "Epidermal growth factor controls smooth muscle alpha–isoactin expression in BC3H1 cells." *Journal of Cell Biology*, vol. 106 No. 3, Mar. 1988, pp. 797–803.
Y. Shing et al. "Purification of a smooth musle cell mitogen from beta tumor cell conditioned medium" *Journal of Cell Biology*, vol. 111, No. 5, part 2 Nov. 1990, p. 227a, abstract No. 1266.

*Primary Examiner*—Jeffrey E. Russel
*Attorney, Agent, or Firm*—David G. Conlin; Gregory D. Williams; David S. Resnick

[57] ABSTRACT

A novel growth factor (BTC-CG) was purified from the conditioned medium of pancreatic beta tumor cells initially derived from transgenic mice (RIP1-Tag2). The purification scheme included BioRex 70 chromatography, phenyl-Sepharose chromatography, TSL-GEL heparin FPLC and C4 reverse phase HPLC. The peptide also stimulated proliferation of bovine smooth muscle cells. It was not inactivated by boiling, by 10 mM dithiothreitol or by exposure to IM acetic acid. Biological activity of BTC-GF was recovered from a single band of protein which had a molecular weight of 2,000 on SDS-PAGE. The Partial N-terminal amino acid sequence of this protein was determined with an ABI 470A protein sequencer as: Asp-Gly-[X]-Thr-[X]-Arg-Thr-Pro-Glu-[X]-Asn-Gly.

10 Claims, 5 Drawing Sheets

SMOOTH MUSCLE MITOGEN

This invention was made with U.S. Government support and the Government has certain rights in the invention.

The present invention is directed to a novel growth factor which stimulates the growth of smooth muscle cells and to the uses thereof.

BACKGROUND OF THE INVENTION

While smooth muscle cell proliferation has been extensively studied, (see, e.g. Schwartz et al., Circulation Research, Vol. 58, No. 4, page 427, the disclosure of which is incorporated by reference herein), the signals controlling the proliferation of smooth muscle cells remain largely unknown. Smooth muscle cell replication is known to play a central role in diseases such as arteriosclerosis (atherosclerosis and hypertension). Lack of smooth muscle proliferation in infants also plays a role in vascular malformations. This failure of smooth muscle cell replication results in untreatable vascular lesions which often lead to death.

Although it is now generally acknowledged that replication of smooth muscle cells occurs during formation of atherosclerotic lesions, the role of that proliferative response in the overall history of the plaque is not all obvious. A few investigators have suggested that replication occurring during development of arteries is the initial event in formation of atherosclerotic lesions, preceding lipid accumulation or endothelial injury.

The major hypothesis explaining smooth muscle replication in the vessel wall is the response-to-injury hypothesis. In brief, hypothesis is that smooth muscle cells in the wall normally exist in a quiescent state. When the endothelium is injured, platelets release a factor or factors that stimulate smooth muscle cell movement into and replication within the arterial intima (Ross Arteriosclerosis 1:293-311, 1981). Ross also showed the cultured smooth muscle cells require a platelet derived growth factor (PDGF) for proliferation (Ross and Glomset N. Eng. J. Med. 295; 369-377 and 420-425, 1976). The apparent conclusion is that platelet release is necessary for smooth muscle proliferative response to balloon denudation.

Ross's observation led to the ensuing purification of the PDGF, identification of its receptor and, more recently, identification of the oncogene c-sis as the gene for one of the two PDGF peptide chains.

The second known requirement for cell cycle progression is availability of somatomedin C., also known as insulin-like growth factor (IGF-1). IGF-1 itself can be synthesized by smooth muscle cells, and antibodies to IGF-1 inhibit cell cycle progression. These data suggest that PDGF is capable of stimulating production of its own progression factor. This observation is of considerable importance to the interesting possibility that smooth muscle replication may be controlled by factors intrinsic to the vessel wall.

Other substances mitogenic for smooth muscle cells, apart from PDGF have also been studied. In addition, platelets also contain a protein resembling epidermal growth factor (EGF) (Oka and Orth, J.Clin. Invest. 72:249-259, 1983) and Assoian et al., 1984) and a factor able to assist growth of cell in suspension called β-tumor growth factor (Tucker et al., Science 226: 705-707, 1984). The relative contribution of each of these to stimulation of proliferation is largely unknown.

The stimuli controlling smooth muscle replication in hypertension also remains largely unknown. PDGF may play an important role in microvascular changes in malignant hypertension, but is not likely to be involved in large vessels or in any vessel affected by milder and more chronic forms of high blood pressure.

While there has been much research on the role of smooth muscle in various disease pathologies, and several mechanisms and roles of growth factors such as PDGF have been explored, there continues to be a need for new information about mitogens which stimulate the proliferation of smooth muscle cells. The identification of such mitogens will permit various treatment strategies to be devised such as competitive binding strategies employing antibodies to the smooth muscle mitogen or competitive proteins which will bind to the receptors for such mitogens. Smooth muscle mitogens may also be used in the treatment of conditions such as vascular malformation or as a growth factor in wound-/ulcer healing.

SUMMARY OF THE INVENTION

In accordance with the present invention, there is provided a novel growth factor (hereinafter "BTC-GF") obtainable from the conditioned medium of pancreatic tumor cells initially derived from transgenic mice (RIP1-Tag 2) in which virtually every beta cell expressed the oncogene SV40 large T. A sample of the pancreatic tumor cells from which BTC-GF was identified, isolated and purified has been deposited at the American Type Culture Collection 12301 Parklawn Drive, Rockville, MD 20852, Oct. 26, 1990 under ATCC Accession No. CLL 10885.

BTC-GF of the present invention is not inactivated by boiling, by 10 mM dithiothreitol or by exposure to 1M acetic acid. The biological activity of BTC-GF is present as a single band of protein having a molecular weight of about 32,000 on SDS-PAGE. The partial N-terminal amino acid sequence of BTC-GF (SEQ ID No:1) is Asp-Gly-Xaa-Thr-Xaa-Arg-Thr-Pro-Glu-Xaa-Asn-Gly.

A computer search based on this amino acid sequence through translated GENBANK and NBRF Protein Database failed to reveal any similar proteins.

BTC-GF of the present invention can be used in the treatment of diseases such as vascular malformation as well as in the treatment of wounds/ulcers and the like. BTC-GF may also be used to produce competitive agents such as antibodies or false peptides. Such competitive agents may be used in the treatment of diseases resulting from smooth cell proliferation such as atherosclerosis and hypertension. It may also be used as a diagnostic test in which an antibody to the growth factor can detect this factor in the blood of diabetics in whom dying or regenerating beta cells with islet are releasing the factor.

DETAILED DESCRIPTION OF THE INVENTION

Figure 1:
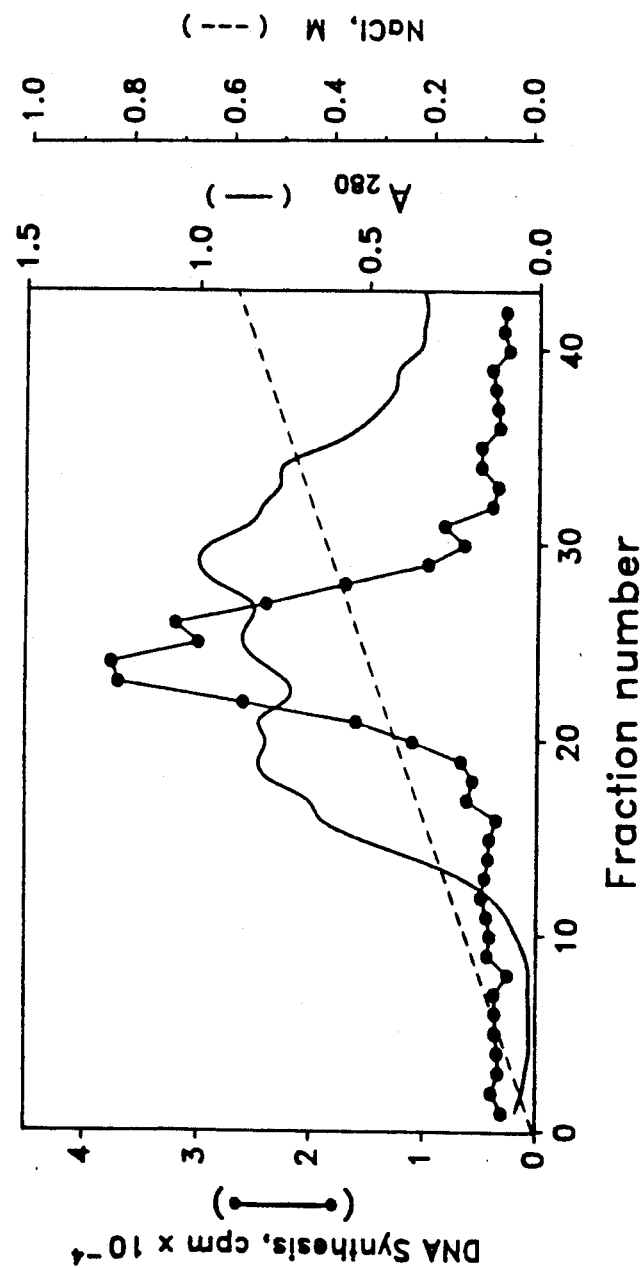
FIG. 1 illustrates the 3T3 cell growth factor activity of BTC-GF after concentrated serum free beta tumor cell conditioned medium is passed through a Biorex 70 Cation Exchange Column.

In accordance with the present invention, there is provided a novel growth factor BTC-GF which promotes the proliferation of smooth muscle cells.

BTC-GF produced in accordance with the present invention has a molecular weight of about 32,000 on SDS-PAGE and is heat stable when subjected to boiling. BTC-GF is also stable in the presence of 10 mM dithiothreitol and when exposed to IM concentration of acetic acid.

BTC-GF was identified and isolated from the conditioned medium of pancreatic tumor cells (ATCC No. CRL 10585, a sample of which was deposited at the American Type Culture Collection under the Budapest Treaty on Oct. 26, 1990) were initially derived from transgenic mice (RIP1- Tag 2) in which virtually every beta cell expressed the oncogene SV40large T.

While a number of methods may be employed in purifying BTC-GF, the preferred method is outlined below and described in more detail in the Examples.

First, the beta tumor cells are cultured in roller bottles in DMEM with 5% calf serum for four days. The medium is then replaced with serum free medium and cultured for 48-72 hours before harvest.

Next, serum free beta tumor cell conditioned medium is concentrated and passed through a number of columns such as a Biorex 70 column, a phenyl sepharose column, and FPLC heparin affinity column, and an HPLC reverse phase column.

Purified BTC-GF of the present invention has a N-terminal amino acid sequence as determined with an ABI 470A protein sequensor of SEQ ID No: 1.

Purified BTC-GF in accordance with the present invention can be used in the treatment of pathological conditions such as vascular malformation by intravascular infusion, or for the treatment of atherosclerosis by administration of a competitive inhibitor.

Purified BTC-GF can also be used in the treatment of wounds, ulcers and the like.

Purified BTC-GF of the present invention can also be used to produce various competitive agents which can be used in the treatment of atherosclerosis and hypertension. Competitive agents such as antibodies or false proteins can be produced which will compete with and/or block BTC-GF from stimulating proliferation of smooth muscle cells.

BTC-GF can also be used to generate antibodies to itself. The antibody generated can be polyclonal or monoclonal depending upon the particular application for which it is designed. Such antibodies can be prepared by techniques well known to the skilled artisan. For example, the protein or antigenic portion thereof can be conjugated to keyhole limpet hemocyanin (KLH) and used to raise an antibody in an animal such as a rabbit. Typically, the peptide-KLH conjugate is injected several times over a period of about two months to generate antibodies. The antibody is then collected from serum by standard techniques. Alternatively, monoclonal antibodies can be produced in cells which produce antibodies to the protein by using standard fusion techniques for forming hybridoma cells. [Kohler, G., et al., Nature 256:495 (1975) which is incorporated by reference]. Typically, this involves fusing an antibody producing cell with an immortal cell line such as a myeloma cell to produce the hybrid cell. Alternatively, monoclonal antibodies can be produced from cells by the method of Huse, et al, Science 246:1275 (1989) which is incorporated herein by reference.

The invention will be further illustrated by reference to the following examples which will aid in the understanding of the present invention, but which are not to be construed as a limitation thereof.

Growth factor activities discussed in the Examples and in Table 1 were assayed by measuring the incorporation of [methyl-$^3$H]thymidine into DNA of quiescent mouse Balb/c 3T3 cells as previously described (Shing Y, Davidson S. and Klagsbrun M. Methods in Enzymology, 146B, 42–48, 1987) the disclosure of which is hereby incorporated by reference.

EXAMPLE 1

Primary cultures of pancreatic beta tumor cells (ATCC Accession No. CRL 10585) were prepared in Dulbecco's modified Eagles medium (DMEM) containing 10% calf serum. These cultures were plated on 162 cm$^2$ cell flasks (Costar Cat #3150) and incubated in a 37° C. humidified CO$_2$ incubator. These cells were used as a source for seeding into 900 cm$^2$-growth-area roller bottles (Costar Cat #3901) containing 125 ml of DMEM with 5% calf serum. The bottles were gased with 90% air/5% CO$_2$ and rotated on a Cell Production Roller Apparatus (Bellco) at 0.5 rpm in a 37° C. incubator. After 4 days the medium in each bottle was replaced with serum-free medium. The medium was harvested and replaced with fresh medium after incubation for 48-72 hours. Six liters of conditioned medium were collected weekly as the starting materials for the purification of growth factors.

EXAMPLE 2

Method for the Purification of BTC-GF

Step 1. Concentration

Ten liters of serum free beta tumor cell conditioned medium were concentrated to 500 ml at 4° C. with an Amicon hollow fiber concentrator using a filter of 10,000 molecular weight cutoff. The concentrated medium was subsequently equilibrated to 50 mM NaCl, 10 mM Tris, pH 7 by continuous dialysis.

Step 2. BioRex 70 Chromatoorophy

The concentrated medium was applied to a BioRex column (200 ml bed volume) equilibrated with 10 mM Tris, pH 7 at 4° C. The column was rinsed with 400 ml of the same buffer and the biological activity was then eluted with a NaCl gradient from 400 ml of 0 M to 400 ml of 0.6 M at a flow rate of 60 ml/hour (FIG. 1).

Step 3. Phenyl-Sepharose Chromatography

Figure 2:
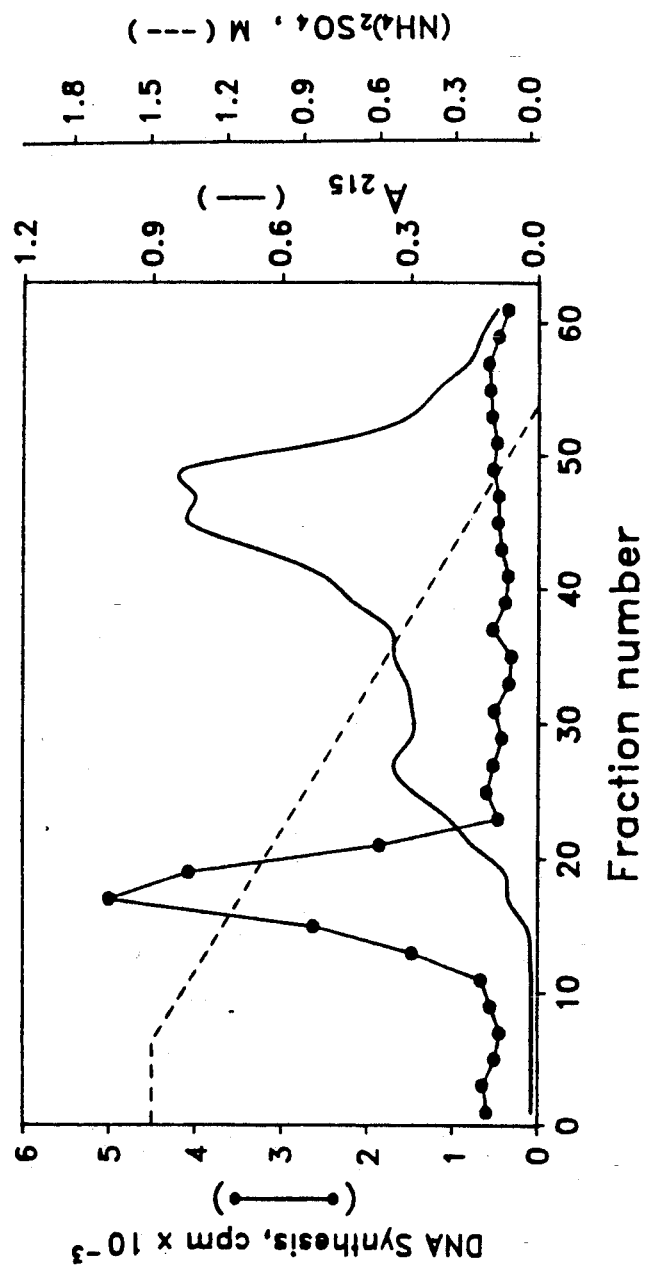
FIG. 2 illustrates the 3T3 cell growth factor activity of pooled active fractions from FIG. 1 when passed through a Phenyl-Sepharose column.

The active fractions from BioRex column were pooled, boiled for 5 minutes and clarified by centrifugation (10,000 x g, 20 minutes). The clear supernatant solution was brought to 1.5M (NH$_4$)$_2$SO$_4$ and applied to a phenyl-Sepharose column (25 ml bed volume) equilibrated at 1.5M (NH$_4$)$_2$SO$_4$, 10 mM potassium phosphate buffer, pH 7 at 4° C. The column was rinsed with 100 ml of equilibration buffer and the biological activity was subsequently eluted with a $(NH_4)_2SO_4$ gradient from 170 ml of 1.5 M to 170 ml of 0M in 10 mM phosphate buffer at pH 7 at a flow rate of 30 ml/hour (FIG. 2).

Step 4. FPLC Heoarin Affinity Chromatography

Figure 3:
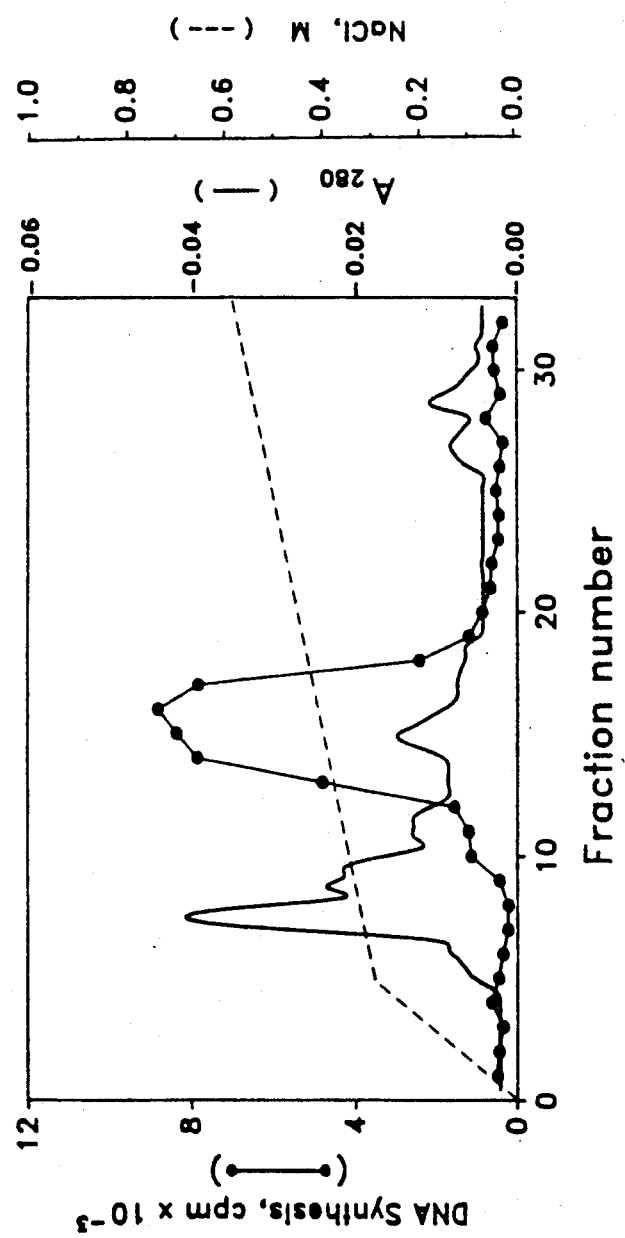
FIG. 3 illustrates the 3T3 cell growth factor activity of the pooled active fractions from the phenyl-sepharose column when passed through an FPLC heparin affinity column.

The active fractions from phenyl-Sepharose column were pooled, dialyzed and applied to TSK-GEL Heparin 5PW glass column (7.5 cm × 8 mm inner diameter) equilibrated with 10 mM Tris, pH 7 at room temperature. The column was rinsed with 10 ml of the same buffer and the biological activity was eluted with NaCl gradient from 0 to 0.3M followed by another NaCl gradient from 0.3 to 0.6M at a flow rate of 1 ml/min/-fraction (FIG. 3).

Step 5. HPLC C4 Reverse Phase Chromatography

Figure 4:
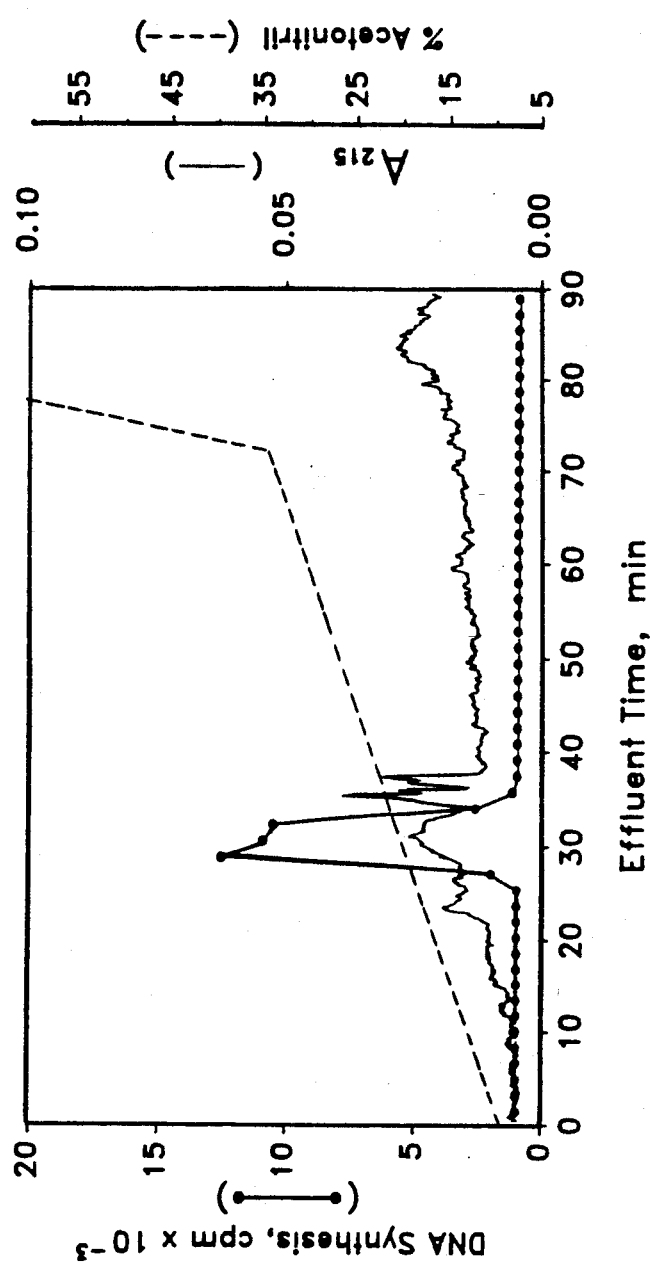
FIG. 4 illustrates the 3T3 cell growth factor activity of the pooled active fractions from the heparin affinity column when passed through an HPLC C4 reverse phase column.
Figure 5:
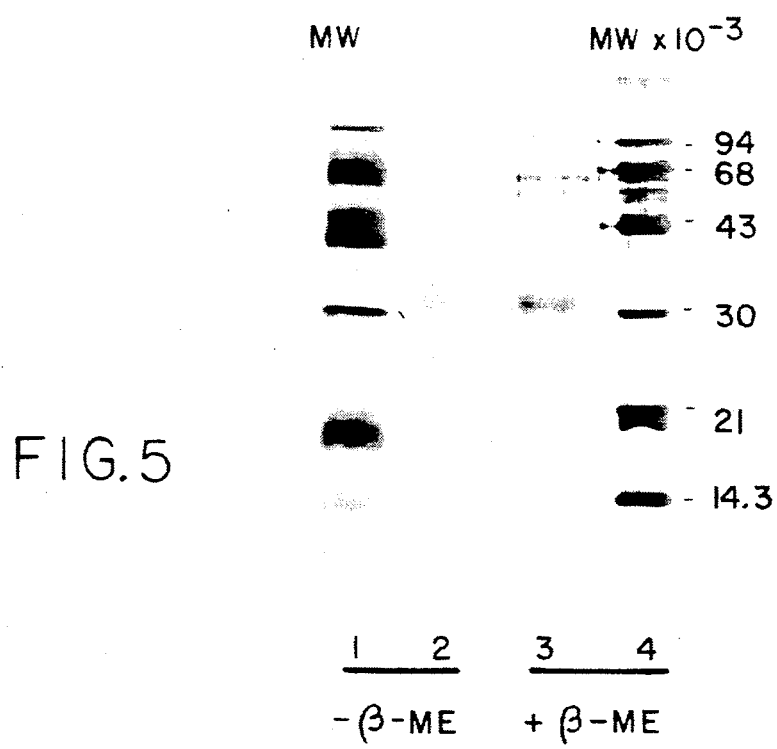
FIG. 5 is a silver strain of BTC-GF an gel from the pooled active fractions obtained by repeating the HPLC C4 reverse phase column purification.

The active fractions from Heparin column were pooled and injected directly into a HPLC reverse phase C4 column equilibrated with 10% acetonitrile in 0.1% TFA at room temperature. The column was rinsed with 20 ml of the same solution and the biological activity was eluted with a gradient of acetonitrile from 10 to 35% at a flow rate of 2 ml/min and fractions of 1.5 ml were collected (FIG. 4). This step was repeated once in order to obtain a silver-stained single band protein on SDS PAGE (FIG. 5).

A summary of the result of purification is shown in Table 1.

TABLE 1

| | Purification of BTC-GF | | | | |
|---|---|---|---|---|---|
| Purification Step | Total Protein, mg | Total Activity, U | Specific Activity, U/mg | Activity Recovery | Purification Fold |
| Conditioned medium | 1360 | $24 \times 10^4$ | $1.7 \times 10^2$ | 100 | 1 |
| BioRex column | 52.7 | $6.5 \times 10^4$ | $1.2 \times 10^3$ | 27 | 7 |
| Heat, 100° C. (5 min.) | 15.5 | $5 \times 10^4$ | $3.2 \times 10^3$ | 21 | 19 |
| Phenyl column | 1.5 | $4 \times 10^4$ | $2.8 \times 10^4$ | 17 | 164 |
| Heparin column | 0.09 | $3 \times 10^4$ | $3.3 \times 10^5$ | 10 | 1,942 |
| C4 column, 1st | 0.0012* | $1.4 \times 10^4$ | $1.2 \times 10^7$ | 5.8 | 70,000 |
| C4 column, 2nd | 0.00034* | $0.98 \times 10^4$ | $2.9 \times 10^7$ | 4 | 170,000 |

Values were based on processing of 10 liters of conditioned medium.
Biological activity was measured by DNA Synthesis in mouse 3T3 cells.
One unit of growth factor activity is defined as the amount of growth factor needed to stimulate half-maximal incorporation of [methyl - $^3$H]thymidine into DNA.
Protein mass was estimated by using $A_{280} = 1.0$ for a 1 mg/ml solution.
*Protein mass was estimated by the intensity of silver stain compared to that of the protein standards and amino acid analysis.

EXAMPLE 3

Mitogenic Acitvity of BTc-GF on Smooth Muscle Cell

Figure 6:
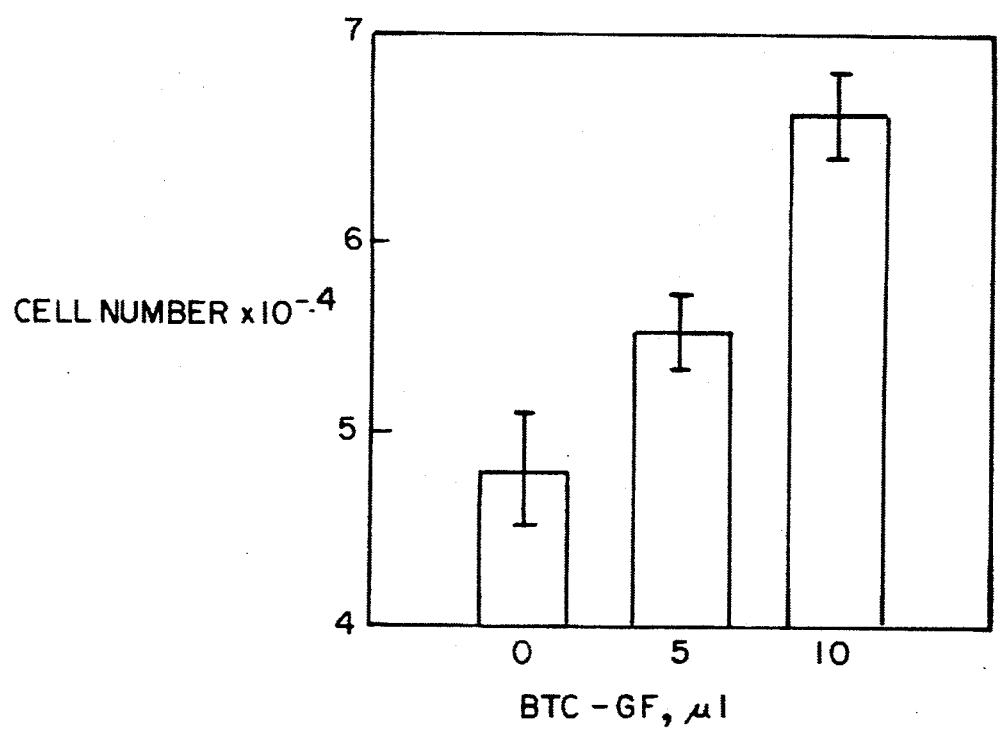
FIG. 6 illustrates the mitogenic activity of BTC-GF on bovine smooth muscle cell.

The purified BTC-GF stimulated the proliferation of bovine aortic smooth muscle cell (SMC) (FIG. 6). The mitogenic activity of BTC-GF was tested on SMC cultured in DMEM containing 1% calf serum. Four days after the test samples were added to the cultures, the cells were trypsinized and the numbers of cells in each well of the 24 well plates were counted with a Coulter Counter.

The protein produced by the above-exampled purification protocol has the following characteristics: BTC-GF is a polypeptide having the N-terminal amino acid sequence depicted in SEQ 10 No: 1. It has a molecular weight of 32,000 as determined by SDS polyacrylamide gel electrophoresis. Its mitogenic activity is not inactivated by exposure to high temperature (100° C., 5 minutes), sulfhydryl reducing agent (10 mM dithiothreitol) or acidic condition (pH 2.2).

What is claimed:

1. A purified protein having an N-terminal amino acid sequence comprising:

SEQ ID No:1, wherein said protein stimulated proliferation of smooth muscle cells.

2. The purified protein of claim 1, wherein the protein is obtainable from beta tumor cells ATCC Accession No. CRL 10585.

3. The purified protein of claim 1, wherein the protein has a molecular weight of about 32,000 on SDS-PAGE.

4. The purified protein of claim 1, having at least about 50% of its activity after heating at 100° C. for 5 minutes.

5. The purified protein of claim 1, wherein said protein is stable when exposed to 1M acetic acid.

6. The purified protein of claim 1, wherein the protein is stable when exposed to 10 mM dithiothreitol.

7. A method for producing the purified protein of claim 1 comprising:

a) concentration serum free beta tumor cell conditioned medium;

b) applying the conditioned medium of step a) to a weakly acidic cation exchange column containing carboxylic acid exchange groups on a macroreticular acrylic polymer lattice;

c) applying active fractions obtained from step b) to a phenyl Sepharose column;

d) applying active fractions obtained from step c) to a heparin affinity column;

e) applying active fractions obtained from step d) to a reverse phase column; and f) collecting active fractions obtained from step e).

8. The method of claim 7, wherein the purified protein produced has a specific activity of about $2.9 \times 10^7$ unit of growth factor activity/mg.

9. A purified polypeptide which includes the amino acid sequence of SEO ID NO:1.

10. The purified protein of claim 1 that is in native form.

* * * * *

UNITED STATES PATENT AND TRADEMARK OFFICE
Certificate

Patent No. 5,229,493                                   Patented: July 20, 1993

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Moses J. Folkman, Brookline; Yuen Shing, Randolph; both of MA; Douglas Hanahan, San Francisco, CA.

Signed and Sealed this Twelfth Day of June, 2001.

BRIAN HEARN
*Senior Petitions Examiner*
Office of Petitions

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 12 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
( A ) ORGANISM: TRANSGENIC MICE (RIP1- Tag2)
( G ) CELL TYPE: PANCREATIC TUMOR CELL ( x i ) SEQUENCE DESCRIPTION: SEQ ID NO:1:

Asp Gly Xaa Thr Xaa Arg Thr Pro Glu Xaa Asn Gly